United States Patent [19]
Cox, deceased et al.

[11] Patent Number: 5,324,658
[45] Date of Patent: Jun. 28, 1994

[54] MEDIA FOR CELL GROWTH AND METHOD FOR MAKING THEM

[75] Inventors: John C. Cox, deceased, late of Catonsville, Md., by Anita Cox, executrix; Hao Chen; Cathryn Kabacoff, both of Columbia, Md.

[73] Assignee: Martek Corporation, Columbia, Md.

[21] Appl. No.: 999,667

[22] Filed: Dec. 30, 1992

Related U.S. Application Data

[63] Continuation of Ser. No. 532,703, Jun. 4, 1990, which is a continuation-in-part of Ser. No. 365,818, Jun. 14, 1989, abandoned.

[51] Int. Cl.$^5$ ............... C12N 1/14; C12N 1/16; C12N 1/20
[52] U.S. Cl. ............... 435/243; 435/253.6; 435/255.1; 435/254.1; 435/255.7; 435/946; 47/1.4
[58] Field of Search ............... 435/41, 68.1, 70.1, 435/71.1, 253.6, 257, 946, 240.1, 243, 253.6, 254.1, 255.7, 946, 255.1; 47/1.4, 1.402

[56] References Cited

U.S. PATENT DOCUMENTS 4,431,738  2/1984  Maeda et al. ............... 435/240.4

FOREIGN PATENT DOCUMENTS 1123838  9/1956  France .

OTHER PUBLICATIONS

Brodin, et al (1989) Protein Engineering 3(5):353-358.
Blake, et al (1961) Journ. Pharm. Sci 50:425-429.
*CRC Handbook of Microalgal Mass Culture* (Richmond, ed.) CRC Press, Inc. Boca Raton, Fla., 1986, pp. 342-352.
*Gibco Laboratories Catalogue and Reference Guide* Grand Island, N.Y., 1987, pp. 172-182.
Davis, et al. *Advanced Bacterial Genetics, a manual for genetic engineering.* Cold Spring Harbor Laboratory, 1980, p. 201.
Torchia, et al., *J. Am. Chem. Soc.*, pp. 2320-2321 (Mar. 30, 1988).
Knirel et al., *Eur. J. Biochem.* 166, pp. 189-197 (1987).
Beutler et al., *J. Natural Products*, 51:3, pp. 562-566 (May-Jun. 1988).
Walker et al., *Applied and Environmental Microbiology*, pp. 92-98 (1987).
Taecker et al., *Biotechnology and Bioengineering, XIII*, pp. 779-793 (1971).
Crespi et al., *Nature*, 184:729 (Aug. 29, 1959).
Crespi et al., "Preparation of Deuterated Proteins and Enzymes", 629-637.
Cox et al., *Tibtech*, vol. 5, Jun. 1987, pp. 279-282.
Delente, *Tibtech*, vol. 5, Jun. 1987, pp. 159-160.
Jakubick et al (1980) Z Ernaehrungsuris 19(1):33-39, Biol Abstr 70(5):3365, Abstract 32087, Sep. 1980.

*Primary Examiner*—Che S. Chereskin
*Attorney, Agent, or Firm*—Rothwell, Figg, Ernst & Kurz

[57] ABSTRACT

Aqueous solutions of partial hydrolysates of algae, optionally labelled with stable isotopes, are used as growth media for cells.

28 Claims, 3 Drawing Sheets

1.5% L-broth — Growth curve

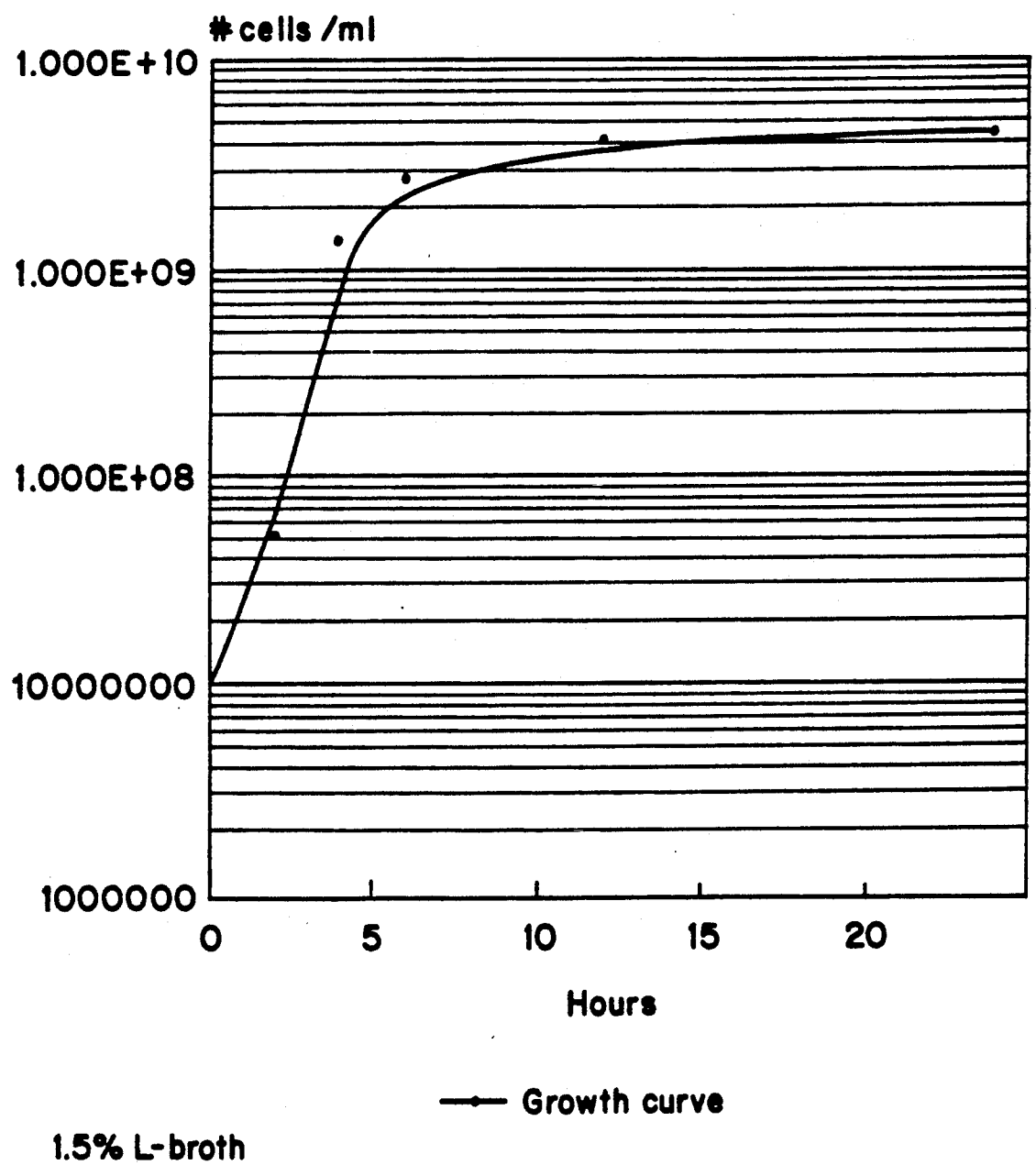

MEDIA FOR CELL GROWTH AND METHOD FOR MAKING THEM

This is a continuation of application Ser. No. 07/532,703, filed Jun. 4, 1990 now abandoned, which is a continuation-in-part of application Ser. No. 365,818, filed Jun. 14, 1989 now abandoned.

FIELD OF THE INVENTION

The present invention is related to novel growth media for procaryotic and eukaryotic cells, including microorganisms, plant, insect and mammalian cells. More specifically, the invention relates to such growth media which comprise hydrolysates of algae which optionally have been labelled with stable isotopes.

BACKGROUND OF THE INVENTION

Many medical and research applications exist today for compounds labelled with stable isotopes. For example, in the areas of structure determination and the elucidation of metabolic pathways, deuterium, $^{13}C$ or $^{15}N$-labelled macromolecules can play essential roles. Labelling with stable isotopes has been used in determining the structure of recombinant proteins (see, for example, Torchia, D. A., et al., *J. Am. Chem. Soc.* 110:2320 [1988]) and the structure and metabolism of polysaccharides from such microorganisms as Streptococcus species and Pseudomonas species (see Wessels, M. R., et al., *J. Biol. Chem.* 262:8262 [1987] and Knirel, Y. A. et al., *Eur. J. Biochem.* 166:189 [1987]). Labelling with stable isotopes also has been used in determining the structure and biosynthesis of antibiotics (see, for example, Beutler, J. A., et al., *J. Natl. Proc. Acad. Sci.* 51:562 [1988]) and in the biosynthesis of labeled tracers, such as amino acids (see Walker, T. E. and R. E. London, *Appl. Env. Microbiol.* 53:92 [1987]).

A practical and convenient way in which to label compounds and macromolecules produced by various microorganisms is to culture the microorganism in a growth medium which contains one or more nutrients labelled with the stable isotope of interest. For example, perdeuterated glucose, which is available commercially, is an excellent substrate for preparing perdeuterated *E. coli.* The high cost of perdeuterated glucose, however, is such that its use is not viable for inexpensive commercial, large-scale media for culturing cells. Accordingly, other labelled substrates capable of supporting growth of desired microorganisms, plant cells and mammalian cells have been sought.

One focus of the investigation has been on algal-based growth media. The terms "algae" and "algal-based" are used herein to denote microalgae, unless otherwise noted. Algal-based growth media have been found to be excellent sources of nutrients for bacteria, able to support rapid growth. Algae grow photosynthetically, with $CO_2$ as the sole carbon source and $H_2O$ as the sole source of hydrogen for cellular material. Several species of algae, such as *Chlorella vulgaris, Chlorella pyrenoidosa* and *Scenedesmus obliquus,* have been shown to grow in 99.9% $D_2O$ (defined herein as pure $D_2O$) with inorganic salts and $CO_2$ as the source of carbon. Under these conditions, deuterium replaces all of the hydrogen in the algae. See, for example, Taecker, R. G., et al., *Biotechnol. Bioeng.* 13:779 (1971). Algae also can grow using 99.9% $^{13}CO_2$ as their carbon source (Behrens, et al., *Journal Applied Phycology,* [1989]) or using $Na^{15}NO_3$ or $K^{15}NO_3$ in place of $NaNO_3$ or $KNO_3$, respectively, as their nitrogen source. As algae are rich in proteins and carbohydrates, algae grown under such conditions incorporate $^2H$, $^{13}C$ or $^{13}N$ uniformly as the corresponding component in the cells. See, for example, Crespi, H. L. et al., *Nature* 184:729 (1959).

The first report in the literature of the development of algal-based growth media for culturing and labelling heterotrophic organisms with stable isotopes was by Blake et al., *J. Pharm. Sci.* 50:425 (1961). Their general procedure for the production of a deuterated-algal-based growth medium involves slurrying deuterated algae with deuterium oxide and then adding the slurry to boiling deuterium oxide to rupture the algal cell walls and release the cellular components. The solution then is cooled and centrifuged, and the residue is extracted with a mixture of methanol and petroleum ether to remove pigments and lipids. The insoluble fraction is dried, then hydrolyzed by refluxing with 1N deuterium chloride for 24 hours. The solution is filtered, the residue discarded, and the hydrolysate then is treated with silver carbonate to remove chloride. The solution is centrifuged and the supernatant is passed through an ion exchange column. The column is washed to remove the nonionic fraction, primarily glucose and mannose. The ionic fraction, comprised primarily of amino acids, then is removed from the column by eluting with 1N HCl.

Although the hydrolysate obtained using this procedure has proved to be a useful medium for culturing and labelling various organisms, further improvements have been sought. The procedure has not been used to make a commercial product, thus researchers wishing to use algal-based growth media must prepare their own growth media from purchased labelled raw materials. Also, the procedure developed by Blake et al. is disadvantageous in that it is expensive, time-consuming and gives inconsistent results according to different laboratory practices. Furthermore, efforts to culture cells of various microorganisms on media prepared in accordance with this procedure often have been unsatisfactory; cell growth has been very limited. Accordingly, it would be highly advantageous to have ready to use, characterized and labelled algal-based growth media that can be inoculated directly by the researcher.

It is an object of this invention to provide a labelled algal-based growth medium that can be used directly by researchers to culture and label various cells and the compounds and macromolecules they produce.

It is a further object of this invention to produce an algal-based growth medium that can support efficient cellular growth.

Further objects of this invention will become apparent from reading the following description of the invention.

SUMMARY OF THE INVENTION

A process for preparing a hydrolysate useful for preparing a substrate for culturing cells comprises:
(a) forming an aqueous slurry of algae,
(b) rupturing the cell walls of said algae,
(c) adding to said algae sufficient acid to form an acid concentration of about 2 to about 3M and then partially hydrolyzing proteins in said algae,
(d) discarding the acid-insoluble fraction from the acid-soluble fraction of the resultant hydrolysate,
(e) removing the acid from the soluble fraction until the fraction has a pH of at least about 1.0, and
(f) titrating the hydrolysate with a base to convert any remaining acid in the hydrolysate to a salt and adjust the pH to within the range of about 6.5 to about 7.0.

The hydrolysate is mixed with water or $D_2O$, filter sterilized, and additional salts and buffers are added as desired to provide a substrate that contains all desired nutrients to support cell growth.

The hydrolysates produced by the method of this invention are suitable as growth media for bacteria, fungi, yeast, and plant and mammalian cells.

In one embodiment of the invention, the algae have been labelled with at least one stable isotope. Cells grown on media based on such labelled algae incorporate the label. Macromolecules or compounds produced by such cells also will have incorporated the label.

BRIEF DESCRIPTION OF THE DRAWINGS

FIG. 3 is a graph showing the growth of *E. coli* cells in 1.0% algal-based growth medium.

DETAILED DESCRIPTION OF THE INVENTION

Figure 1:
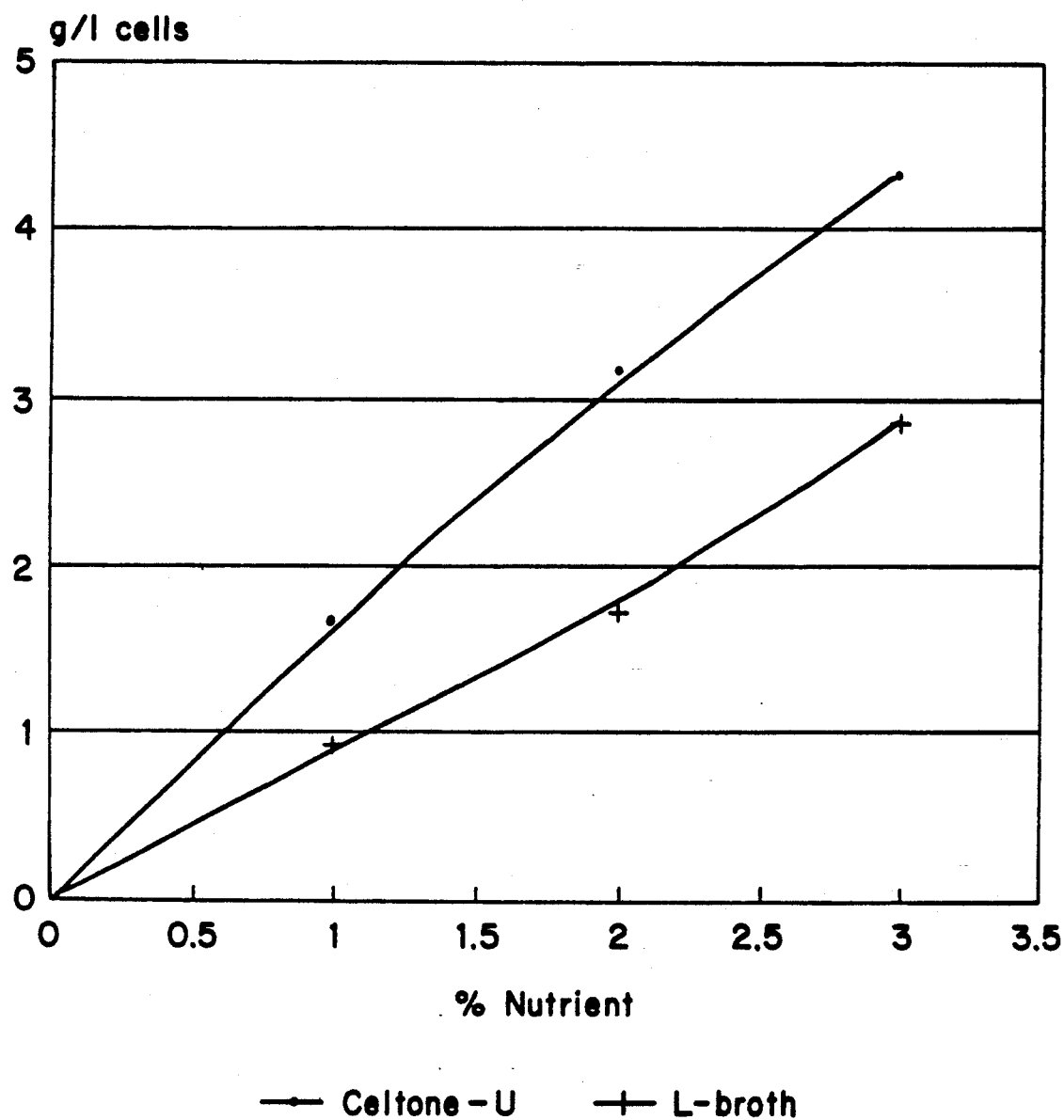
FIG. 1 is a graph showing the yield of *E. coli* cells grown in each of several concentrations of an algal-based growth medium of this invention and corresponding concentrations of L-broth.

In accordance with the process of the present invention, algal-based growth media are produced which can be used as substrates for the growth of a wide variety of cells, including bacteria, yeast, fungi, insect cells, plant cells and mammalian cells. In one embodiment of the invention, the algae that are processed to produce the growth media have been labelled with stable isotopes.

To prepare the growth media of this invention, algae can be cultured in accordance with conventional procedures. Advantageously, the algae can be cultured in a photobioreactor which provides for even distribution of light throughout an agitated medium. A wide variety of species of algae can be used to make the growth media of this invention. Suitable algae include species of Chlorella, Navicula, Neochloris, Scendesmus, Porphorydium, Dunalliela, Spirulina and Chlamydomonas, including *Chlorella vulgaris*, *Navicula saprophila*, *Neochloris oleoabundans* and *Scenedesmus obliquus*.

If it is desired to use algae that have been labelled with one or more stable isotopes, the growth medium for the algae includes inorganic sources of the desired isotope(s) as the sole source of the element. Stable isotopes that can be incorporated into the algae include $^2H$, $^{13}C$, $^{15}N$ and $^{17}O$. As discussed above, the labelling of algae with one or more of these stable isotopes is known in the art.

As noted above, a convenient carbon source for algal growth is $CO_2$. During cultivation, as the carbon is metabolized, the pH of the culture medium will rise. The pH of the medium desirably is kept at about 7.8. When the pH reaches about 8.0, enough additional $CO_2$ is bubbled through the medium to return the pH to about 7.8.

Photosynthesis generates oxygen ($O_2$), which preferably is removed periodically, desirably when the pH reaches 8.0 (i.e., just before $CO_2$ addition). If the algae are grown in a photobioreactor, the photobioreactor can be opened by the use of solenoid valves and the $O_2$ removed in an exhaust stream. If desired, the exhaust stream can be passed through a 2M KOH solution to trap any $CO_2$ that could have co-exhausted. This step may be desirable if the carbon in the $CO_2$ is labeled.

Once the algae have been cultured to a desired density, they are harvested in accordance with conventional procedures. An aqueous slurry of the cells then can be treated to lyse the cell walls, if lysis has not occurred as part of the harvesting process. Lysis can be carried out in accordance with any conventional procedure, such as, but not limited to, adding the slurry to boiling water and then centrifuging to remove the liquid or by mechanical breaking, including sonification and French press, or any other method known to those skilled in the art. Mechanical breaking is preferred.

The resultant cell debris then is treated with acid to partially hydrolyze the protein fraction of the algae. Hydrolysis conditions are selected such that the proteins are not completely hydrolyzed to substantially all individual amino acids. The hydrolysis is carried out under conditions such that the resultant hydrolysate comprises small polypeptides as well as free amino acids. Advantageously, at least about 35% by weight of the resultant hydrolysate, and preferably about 40% to about 50%, comprises small polypeptides, the polypeptides typically comprising about 2-10 amino acids. Although not wishing to be bound by theory, it appears that growth media containing small peptides may support more cell growth than comparable media containing single amino acids; some peptides appear to be more readily absorbed by cells than free amino acids.

Such partial hydrolysis can be accomplished, for example, using a gentle acid hydrolysis. This can comprise adding an acid to the aqueous slurry of algae to bring the slurry to a final acid concentration of about 2 to 3M, preferably about 2.5M, stirring the acidified slurry to begin the hydrolysis and then heating to boiling to increase the efficiency of the reaction. A preferred acid is HCl, although other acids, including sulfuric acid and trifluoroacetic acid, also can be used. Generally, it has been found that heating and refluxing for a period of about 2-4 hours is sufficient to hydrolyze the proteins to the desired extent.

Once the hydrolysis reaction has been completed, the fraction of the algae that is insoluble in the acid is separated from the soluble fraction and discarded. The insoluble fraction contains mainly lipids and pigments. The soluble fraction of the hydrolysate comprises primarily sugars, amino acids, and the partially hydrolyzed protein (i.e., the peptides).

The acid then is removed from the soluble fraction. Conveniently, as an initial step, the fraction is heated under vacuum to evaporate much of the acid. The resulting slurry can be resuspended in water and more acid can be evaporated. This procedure can be repeated one or more times if necessary until a pH of at least about 1.0 is obtained.

The hydrolysate then is titrated with a base until the pH of the hydrolysate is raised to within the range of about 4-9, preferably about 6.5 to 7. Conveniently, if the acid used in the hydrolysis reaction was HCl, the base selected is NaOH; addition of the base, upon neutralizing the acid, forms sodium chloride, a desired component in the final hydrolysate. Other bases that can be used include KOH, $Ba(OH_2)$ and $BaCO_3$. The acid soluble hydrolyzate can be clarified.

The neutralized hydrolysate is concentrated. This can be accomplished by any conventional method, including freeze-drying, rotary evaporation or oven drying. The resulting product is a hygroscopic particulate solid.

Media solids made by the process of this invention can comprise about 35% to about 50% small peptides, about 22% to about 30% amino acids, about 5% to about 15% total reducing sugars and sugars (primarily aldohexose and trace amounts of ketohexose, respectively) and about 7% to about 15% water. Preferably they comprise about 40% to about 45% peptides, about 24% to about 28% amino acids, about 5% to about 15% reducing sugars, and about 7% to about 15% water.

To make the final formulation, the hydrolysate is added to water, centrifuged to remove insoluble material and sterilized such that the resultant medium is about 0.25% to about 10% hydrolysate, preferably about 1.0% hydrolysate. Additional salts and buffers can be added to the medium as desired to provide a final product that contains all desired nutrients for supporting cell growth. For example, one liter of growth medium typically comprises about 2.5 to about 100 g, preferably about 13 g., of the algal hydrolysate, about 1.5 to about 2.0 g, preferably about 1.8 g, of potassium diphosphate, and about 1.0 to about 1.8 g, preferably about 1.4 g, potassium monophosphate. The hydrolysate is centrifuged to remove insoluble material and filter sterilized.

Other salts, including magnesium sulfate, typically in the range of about 0.2 to about 1.2 g, ammonium chloride, typically in the range of about 0.8–1.2 g, and calcium chloride, typically 0.1 ml of 1M $CaCl_2$, also can be added per liter of the medium. Additional salts that can be added in conventional amounts include iron sulfate and inorganic salts of manganese, molybdenum, cobalt, copper and zinc.

If desired, supplemental carbohydrates can be added to the final formulation. Such carbohydrates can include, for example, glucose, glycerol, fructose, or other commonly available carbon source. The carbohydrate can be labeled with a stable isotope and added to the hydrolysate in the form of a sterile concentrated solution. Supplementation of the hydrolysate with carbohydrates prior to its use as a growth medium provides an additional energy source and may be desirable to achieve greater cell density or to maximize the desired product.

The resulting product can be used as a substrate to support the growth of bacteria, such as $E.\ coli$, $B.\ subtilis$ and $S.\ aureus$; yeasts, such as $Candida\ lipolytica$; fungi, including Apiotrichum and Rhizopus, plant cells, insect cells and mammalian cells.

Media made using the hydrolysates of this invention have been found to support the rapid and efficient growth of cells. If the algae used as the basis for forming the hydrolysates have been labelled with one or more stable isotopes, the subsequent cells and the compounds or macromolecules they produce incorporate the label(s).

The present invention is further illustrated by the following examples, which are provided for illustrative purposes only and are not intended to be limiting.

EXAMPLE 1

Cultivation of Algae $Chlorella\ vulgaris$, Culture Collection of Algae and Protozoa, United Kingdom, CCAP No. 211-8, available commercially, is grown in a mineral salts medium consisting of 0.1 g/l $K_2HPO_4$, 0.075 g/l $KH_2PO_4$, 0.5 g/l $MgSO_4 \cdot 7H_2O$, 0.0625 g/l $Ca(NO_3)_2 \cdot 4H_2O$, 3.0 g/l $KNO_3$, 10 mg/l $FeSO_4 \cdot 7H_2O$, 8.0 mg/l disodium EDTA, 2.86 mg/l $H_3BO_3$, 1.81 mg/l $MnCl_2 \cdot 4H_2O$, 0.22 mg/l $ZnSO_4 \cdot 7H_2O$, 0.39 mg/l $Na_2MoO_4 \cdot 2H_2O$, 0.08 mg/l $CuSO_4 \cdot 5H_2O$ and 0.05 mg/l $Co(NO_3)_2 \cdot 6H_2O$. The vessel used is a 130 liter photobioreactor. The optimal temperature for growing this algae is 32°–35° C. The pH is maintained at 7.0 by the addition of carbon dioxide. The culture is mixed by a continuous flow of air.

$Chlorella\ vulgaris$ grows at a maximum rate of four doublings per day. The culture is harvested at the point at which the nitrogen source has been depleted. For every gram of $KNO_3$ used, about 2 g of dried biomass will be produced.

Cultures are harvested; the algal biomass is suspended in water to about 10–15% solids (w/w). The cells then are mechanically broken.

Example 2

Cultivation of Labelled Algae

Cultivation of $Chlorella\ vulgaris$ labelled with stable isotopes for the production of isotopically labelled growth media is carried out as set forth in Example 1 above, except:

for $^{15}N$ labelled algae, labelled $KNO_3$ is used in place of $KNO_3$;

for deuterated algae, $D_2O$ is used in place of water and air, bubbled through for mixing, is dried in a molecular sieve;

for $^{13}C$ labelled algae, the pH is maintained between 8.0 and 8.5, and $^{13}C$-enriched $CO_2$ is used in place of $^{12}C\ CO_2$.

EXAMPLE 3

Preparation of Acid Hydrolysate from Freeze-dried Biomass

Five grams of dried, broken biomass from $C.\ vulgaris$, made in accordance with the procedure of Example 1, is placed in a round bottom flask. To this biomass is added 50 ml of 2.5M HCl. The mixture is allowed to stir at room temperature (25° C.) overnight. The algal slurry is heated to boiling (with stirring) and allowed to reflux for 2 hours. The slurry then is centrifuged and the acid insoluble fraction is discarded. The percent of biomass which is solubilized by the acid is about 69%. Much of the acid then is evaporated by rotary evaporation. The slurry is resuspended in water to remove remaining acid by additional evaporation. The amount of acid removed during any cycle is limited by the HCl, $H_2O$ azeotrope. This procedure is repeated four times so that more than 90% of the acid is removed, then the slurry is resuspended in water. The pH is about 1.2. 4M NaOH is added to the hydrolysate to a final pH of 6.8. The amount of base added is used to calculate the amount of sodium chloride formed. The hydrolysate then is freeze-dried and weighed. The calculated amount of salt is subtracted from the weight; this final weight (-salts) then is used to make a 1% (w/w) salt-free solution of acid hydrolysate in water.

EXAMPLE 4

Preparation of Media from 1% Solution Acid Hydrolysate

To one liter of the 1% hydrolysate produced as in Example 3, are added 1.8 g $K_2HPO_4$, g $KH_2PO_4$ and 1.0 g $NH_4Cl$. The hydrolysate then is centrifuged. To the supernatant then is added 1.0 g $MgSO_4$ and 0.1 ml 1M CaCl$_2$. The media then is filter sterilized and is ready to use.

EXAMPLE 5

Growth Kinetics of *E. coli* with Algal-based Growth Media and with L-Broth

An inoculum for *E. coli* strain W3110, a mutant derivative of *E. coli* K12 (J. Lederberg et al., University of Wisconsin) was prepared by taking a loopful of *E. coli* and inoculating 15 ml of growth media. This inoculum was shaken overnight (12 hours) at 37° C. Flasks were set up as follows:

| Number of flasks | Growth Media | % of Nutrients in Media |
|---|---|---|
| 3 | Algal-based hydrolysate | 1% |
| 3 | Algal-based hydrolysate | 2% |
| 3 | Algal-based hydrolysate | 3% |
| 3 | L-broth | 1% |
| 3 | L-broth | 2% |
| 3 | L-broth | 3% |

Each flask contained 15 ml. of media. The algal based media was made in accordance with the preceding examples; the L-broth made from 10 g/l tryptone, 5 g/l yeast extract, 10 g/l NaCl. 0.02 ml. of inoculum were added to each flask. All samples were done in triplicate. The flasks were shaken at 37° C. and 1 ml samples were removed asceptically at 2, 4, 6, 12 and 24 hours. The optical density was read at wavelength of 550 by a spectrophotometer. The cell number was calculated by use of the relationship that an OD of $1=2\times10^8$ cells/ml. Upon collection of the last timepoint, the *E. coli* was centrifuged and freeze-dried, and the weight of the dried biomass was recorded. The dry weight at 1%, 2% and 3% algal hydrolyzate, matched by the equivalent L-broth nutrients, are shown in FIG. 1.

Figure 2:
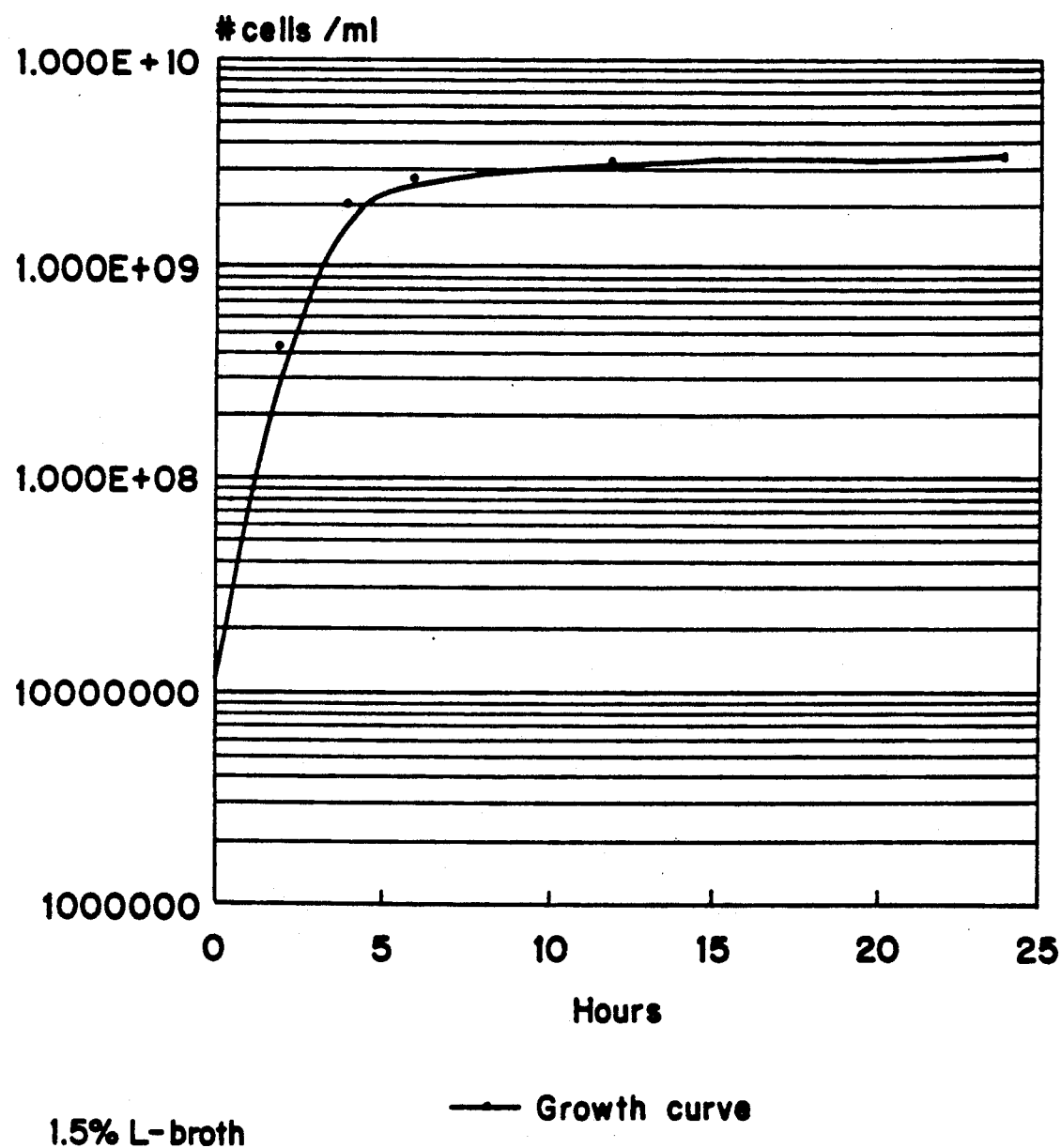
FIG. 2 is a graph showing the growth of *E. coli* cells in 1.5% L-broth.

L-broth also was prepared containing 1.5% nutrients and *E. coli* cells were grown in this medium as above. The growth kinetics of *E. coli* in growth medium (1.0% nutrients) and L-broth (1.5% nutrients) are shown in FIGS. 2 and 3. As can be seen from the figures, after 24 hours of growth the algal-based medium supported the growth of more cells/ml. at 1.0% nutrients than did the L-broth at 1.5% nutrients.

EXAMPLE 6

Growth Kinetics of *E. coli* in Stable Isotopically Labelled Growth Media and L-Broth The method for determining the growth kinetics using isotopically labelled media (obtained using labelled algal biomass as in Example 2 and the growth medium preparation procedures of Examples 3 and 4) is the same as in Example 5. The cell number/ml and dry weights are similar. Deuterated *E. coli* shows a pronounced isotope effect upon growth rate. The growth rate is between 2-5 times slower than its unlabelled counterpart.

We claim:

1. A process for preparing an algal-based hydrolysate which comprises:
   (a) forming an aqueous slurry of algae,
   (b) rupturing the cell walls of said algae,
   (c) adding to said algae sufficient acid to partially hydrolyze proteins in said algae, such that the resultant hydrolysate comprises 35%–50% by weight small polypeptides and 22%–30% amino acids, the resultant hydrolysate comprising an acid-soluble fraction and an acid-insoluble fraction,
   (d) discarding the acid-insoluble fraction of the hydrolysate,
   (e) removing acid from the soluble fraction until the fraction has a pH of at least 1.0, and
   (f) titrating the hydrolysate with a base to convert any remaining acid in the hydrolysate to a salt and adjust the pH of the hydrolysate to within the range of about 6.5 to about 7.0.

2. The process of claim 1, wherein the algae has been labelled with one or more stable isotopes.

3. The process of claim 1, wherein the resultant hydrolyzate is dried.

4. The process of claim 2, wherein the isotopes are selected from $^2$H, $^{13}$C, $^{15}$N and $^{17}$O.

5. The process of claim 1 or 2, wherein the hydrolysate is formed into an aqueous solution useful for supporting growth of bacterial, yeast or fungal cells, the aqueous solution further comprising one or more salts and buffers which provide additional nutrients for cell growth.

6. The process of claim 5, wherein the buffer is phosphate buffer.

7. The process of claim 5, wherein the salts are selected from ammonium chloride, sodium chloride, calcium chloride, magnesium sulfate, iron sulfate, and inorganic salts of manganese, molybdenum, copper, cobalt and zinc.

8. The process of claim 1, wherein the acid is added to the algae to form an acid concentration of about 2 to about 3M.

9. The process of claim 1, wherein the acid is selected from HCl and sulfuric acid and trifluoroacetic acid.

10. The process of claim 1, wherein the acid is HCl.

11. The process of claim 1, wherein the base is selected from NaOH, KOH, Ba(OH)$_2$ and BaCO$_3$.

12. The process of claim 1, wherein the acid is HCl and the base is NaOH.

13. The process of claim 1, wherein the algae is selected from species of Chlorella, Neochloris, Navicula Scenedesmus, Spirulina, Chlamydomonas, Porphoridium and Dunalliela.

14. The process of claim 13, wherein the algae is *Chlorella vulgaris*.

15. The process of claim 5 wherein the hydrolysate comprises about 0.25% to about 10.0% of the solution.

16. A nutrient medium for the cultivation of bacterial yeast or fungal cell cultures prepared by a process which comprises:
   (a) growing algal cells,
   (b) forming an aqueous slurry of the cells,
   (c) disrupting the cells to produce a cell lysate,
   (d) subjecting the cells or cell lysate to acid hydrolysis under conditions that result in incomplete hydrolysis of cellular proteins to produce a partial hydrolyzate; the hydrolysate comprising an acid-soluble fraction, which comprises about 35% to about 50% by weight small polypeptides and about 22% to about 30% amino acids, and an acid-insoluble fraction;
   (e) discarding the acid-insoluble fractions;
   (f) removing acid from the soluble fraction until the fraction has a pH of at least about 1.0 and then titrating the fraction with a base to within the range of about 6.5 to about 7.0,
   (g) optionally adding one or more trace minerals or nutrients to the partial hydrolyzate.

17. A nutrient medium for the cultivation of bacterial, yeast or fungal cell cultures prepared by a process which comprises:
(a) growing algal cells which have been labelled with at least one stable isotope,
(b) forming an aqueous slurry of the cells,
(c) disrupting the cells to produce a cell lysate,
(d) subjecting the cells or cell lysate to acid hydrolysis under conditions that result in incomplete hydrolysis of cellular proteins to produce a partial hydrolysate, the hydrolyzate comprising an acid soluble fraction, which comprises about 35% to about 50% by weight small polypeptides and about 22% to about 30% amino acids, and an acid insoluble fraction,
(e) discarding the acid insoluble fraction,
(f) removing acid from the soluble fraction until the fraction has a pH of about 1.0 and then titrating the fraction with a base to within the range of about 6.5 to about 7.0,
(g) optionally adding one or more trace minerals or nutrients to the partial hydrolysate.

18. An algal-based hydrolysate which comprises:
(a) about 35 to about 50% by weight polypeptides,
(b) about 22 to about 30% amino acids,
(c) about 5 to about 15% sugars and reducing sugars and
(d) about 7 to about 15% water.

19. The hydrolysate of claim 18, which comprises:
(a) about 40 to about 45% by weight polypeptides;
(b) about 24 to about 28% by weight amino acids;
(c) about 5 to about 15% by weight sugars and reducing sugars, and
(d) about 7 to about 15% by weight water.

20. The hydrolysate of claim 17, made from algae which has been labelled with one or more stable isotopes.

21. The growth medium of claim 16 or 17, supplemented with glucose, glycerol or fructose.

22. A substrate for supporting bacterial, yeast or fungal cell growth which comprises an aqueous solution of the hydrolysate of claim 18, said hydrolysate comprising about 0.25 to about 10% of said substrate.

23. A process according to claim 5, wherein the aqueous solution formed is useful for supporting bacterial cell growth.

24. A program according to claim 5, wherein the aqueous solution formed is useful for supporting yeast cell growth.

25. A process according to claim 5, wherein the aqueous solution formed is useful for supporting fungal cell growth.

26. A substrate for supporting bacterial cell growth which comprises an aqueous solution of the hydrolysate of claim 18, said hydrolysate comprising about 0.25 to about 10% of said substrate.

27. A substrate for supporting yeast cell growth which comprises an aqueous solution of the hydrolysate of claim 18, said hydrolysate comprising about 0.25 to about 10% of said substrate.

28. A substrate for supporting fungal cell growth which comprises an aqueous solution of the hydrolysate of claim 18, said hydrolysate comprising about 0.25 to about 10% of said substrate.

* * * * *

UNITED STATES PATENT AND TRADEMARK OFFICE
CERTIFICATE OF CORRECTION

PATENT NO. : 5,324,658
DATED : June 28, 1994
INVENTOR(S) : John C. Cox, deceased, et al.

It is certified that error appears in the above-indentified patent and that said Letters Patent is hereby corrected as shown below:

Col. 8, line 48, after "bacterial" insert a comma; col. 10, line 16, "program" should be --process--.

Signed and Sealed this

Eleventh Day of October, 1994

Attest:

BRUCE LEHMAN

*Attesting Officer*    *Commissioner of Patents and Trademarks*